US 6,644,853 B1

(12) United States Patent
Kantor et al.

(10) Patent No.: US 6,644,853 B1
(45) Date of Patent: Nov. 11, 2003

(54) X-RAY TUBE HEAD WITH IMPROVED X-RAY SHIELDING AND ELECTRICAL INSULATION

(76) Inventors: Arkady Kantor, 2143 Silver Linden La., Buffalo Grove, IL (US) 60089; John Griser, 424 Rambler Pl., Streamwood, IL (US) 60107

( * ) Notice: Subject to any disclaimer, the term of this patent is extended or adjusted under 35 U.S.C. 154(b) by 0 days.

(21) Appl. No.: 10/116,930

(22) Filed: Apr. 5, 2002

(51) Int. Cl.[7] ............................................... H01J 35/16
(52) U.S. Cl. ....................... 378/203; 378/121; 378/193
(58) Field of Search ................................. 378/203, 119, 378/121, 167, 168, 169, 170, 193, 197, 189, 190, 191, 196

(56) References Cited

U.S. PATENT DOCUMENTS

| | | | | |
|---|---|---|---|---|
| 4,024,405 A | | 5/1977 | Szot ........................ 250/516.1 |
| 4,104,530 A | | 8/1978 | Weiss ........................... 378/38 |
| 4,104,532 A | | 8/1978 | Weiss ........................... 378/38 |
| 4,127,776 A | | 11/1978 | Pickel ......................... 378/156 |
| 4,157,476 A | * | 6/1979 | O'Connor ................... 378/203 |
| D290,500 S | * | 6/1987 | Makas et al. .............. D24/158 |
| 4,893,321 A | * | 1/1990 | Eitner et al. ................. 378/121 |
| 4,984,261 A | | 1/1991 | Maldonado et al. ........ 378/202 |
| D387,163 S | * | 12/1997 | Osthues et al. ............ D24/158 |
| D470,589 S | * | 2/2003 | Choi et al. ................. D24/158 |

* cited by examiner

Primary Examiner—Drew A. Dunn
Assistant Examiner—Courtney Thomas
(74) Attorney, Agent, or Firm—Godfrey & Kahn, S.C.

(57) ABSTRACT

A dental x-ray tube head having a housing with an x-ray tube mounted in it, with improved shielding for preventing stray radiation from emanating outside of the path of the primary x-ray beam. The shielding includes an inner hollow element encasing the x-ray tube and having an aperture through which the primary beam projects, with an open end for connecting wires to the x-ray tube. The shielding further includes an outer hollow element which fits over the inner element in such a way as to cover the open end, with clearance for the wires connected to the tube. Both the inner element and the outer element are comprised of a mixture of polypropylene and barium sulfate. The combination of the inner element and the outer element completely surrounds the x-ray tube with the barium sulfate impregnated material, eliminating the use of lead within the tube head, and thereby providing excellent electrical insulation characteristics besides the x-ray attenuation.

3 Claims, 4 Drawing Sheets

X-RAY TUBE HEAD WITH IMPROVED X-RAY SHIELDING AND ELECTRICAL INSULATION

BACKGROUND OF THE INVENTION

This invention pertains to improvements in apparatus for performing dental x-ray examinations. The invention features a better way to shield a dental x-ray tube head for preventing emanation of unwanted stray radiation, while still retaining effective insulation against the high voltages produced within the x-ray tube.

Dental x-ray apparatus customarily has the x-ray tube enclosed in an oil-filled housing called a tube head. One face of the tube head has an opening through which the primary x-ray beam is projected from the x-ray tube target toward the examination subject. A tubular member, called a cone, is coupled to the tube head axially of the opening to assist in aiming the x-ray beam at the proper zone on the subject's face. Early in this art, the x-ray tube head or housing had been completely lined with an x-ray shield such as sheet lead to prevent the stray radiation, that is, radiation other than that in the primary beam, from emanating in all directions through the walls of the housing. Most of the sheet lead is usually disposed on the inside wall of the housing so that it encloses a volume which is substantially the same as the volume of the housing. One reason for arranging the lead sheet in this way is to avoid having it be too close to the x-ray tube and other components in the tube head which have high voltage, in the range of 70 to 100 KV, applied to them.

The use of lead for shielding results in a tube head that has undesirably great weight and size. A consequence is that the pantograph type of tube head support arm, which is usually used to support the tube head for movement with all degrees of freedom, must be designed for handling the unduly high weight. It is more difficult to support a heavy tube head in such manner that it will remain in equilibrium when positioned near the patient than it is to support a lighter tube head.

To date, the conventional solution to the problem of excessive weight of lead shielding is partially exemplified in O'Connor, U.S. Pat. No. 4,157,476. O'Connor shows a dental x-ray tube head wherein the x-ray tube is partially enclosed by a member formed of a resin impregnated with barium sulfate. The resin shielding member, however, is open in several areas. Besides the side area from which the intended x-ray beam is to be emitted, the resin shielding member is also open at the end, to permit the connection of wires. It was found in putting the O'Connor arrangement to actual use that the insulating oil had insufficient x-ray attenuation properties to be relied upon to stop the x-radiation from escaping from the open end of the resin shielding member.

Various solutions have been attempted to resolve this latter problem. One solution was to manufacture the outer casing of zinc, rather than the aluminum admitted by O'Connor to have poor x-ray attenuating properties. Zinc, however, has a severe weight disadvantage when compared to aluminum. Another solution attempted was to manually form a lead shield over the open end of the resin shielding member. As indicated in O'Connor, though, lead is toxic and is a health hazard to persons involved in making the shield. Moreover, when pieces of lead sheet are used for shielding, there is a greater chance for radiation to leak through a joint. Even further, lead shielding is an electrical conductor, requiring the addition of electrical insulation, or at least an increase of spacing, surrounding the lead shielding. Lead shielding can also cause air bubbles to form in the insulating oil, again reducing the electrical insulation and radiation shielding.

This invention relates to improvements to the apparatus described above, and solutions to the problems raised and/or not solved thereby.

BRIEF SUMMARY OF THE INVENTION

In accordance with the invention, in a dental x-ray tube head comprising a housing having an x-ray tube mounted in it, there is improved shielding for preventing stray radiation from emanating outside of the path of the primary x-ray beam. The shielding includes an inner hollow element encasing the x-ray tube and having an aperture through which the primary beam projects, with an open end for connecting wires to the x-ray tube. The shielding further includes an outer hollow element which fits over the inner element in such a way as to cover the open end, with clearance for the wires connected to the tube. Both the inner element and the outer element are comprised of a mixture of polypropylene and barium sulfate. The combination of the inner element and the outer element completely surrounds the x-ray tube with the barium sulfate impregnated material, eliminating the use of lead within the tube head, and thereby providing excellent electrical insulation characteristics besides the x-ray attenuation. This combination also permits the tube head casing to be formed of aluminum rather than zinc, with the all the weight advantages attendant thereto.

These and other objects and advantages of the present invention will become apparent from the detailed description, claims, and accompanying drawings.

DESCRIPTION OF THE INVENTION

Figure 1:
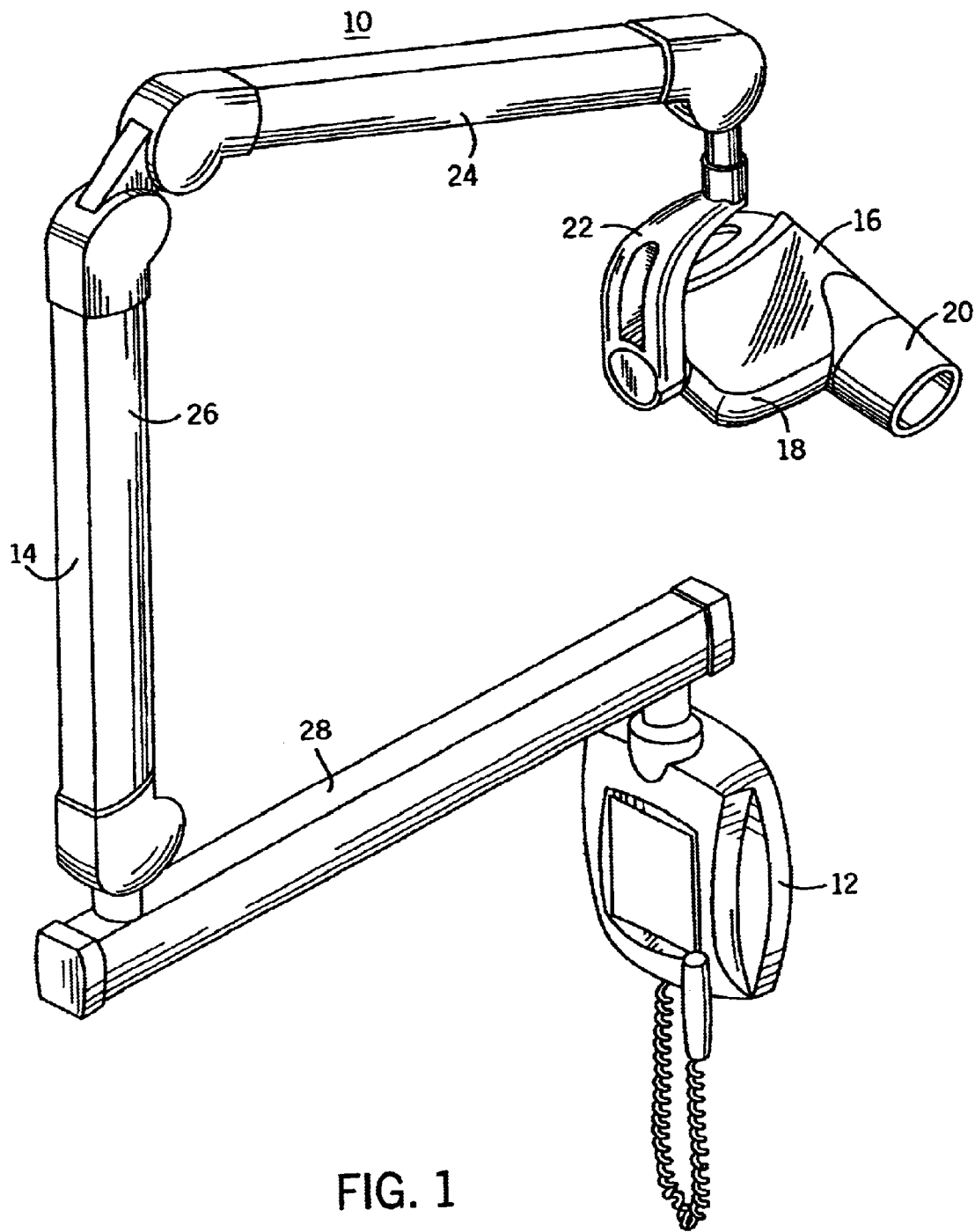
FIG. 1 is a perspective view of a dental x-ray tube head and its supporting arm mechanism.

As shown in FIG. 1, a dental x-ray apparatus 10 includes a wall unit 12 as a source of power, an articulated arm assembly 14 connected at one end to the wall unit, and a tube head 16 connected to the opposite end of the arm assembly. The dental x-ray tube head 16 includes a tube end wall 18 to which a tubular assembly 20, also known as a cone, is attached or formed integrally. The tube head 16 is connected to the end of the arm assembly 14 by a yoke 22 which allows the head to rotate about a first axis at the point where the yoke attaches to the head, while at the same time permitting rotation of the head about a second, transverse axis at the point where the yoke attaches to the arm. Yoke 22 is pivotably mounted to a first end of a first arm segment 24 of articulated arm assembly 14, which in turn is pivotably connected at its opposite end to a second arm segment 26. The latter is mounted for rotation about a vertical axis on the distal end of a horizontally swingable arm segment 28, which in turn rotates about a vertical axis at its proximal end at the wall unit 12. The wall unit 12 contains the x-ray tube controller (not shown) and is symbolized by a prism shaped box. This box may be mounted on a wall in the examination room in proximity with the chair on which the examination subject rests. It will be apparent that the articulated arm assembly 14 for the tube head 16 which has just been described may take many different forms and still enable the tube head 10 to be advanced, retracted and positioned as desired relative to the examination subject. The functional features of the tube support in general, including the articulated arm assembly 14, are essentially conventional.

Figure 2:
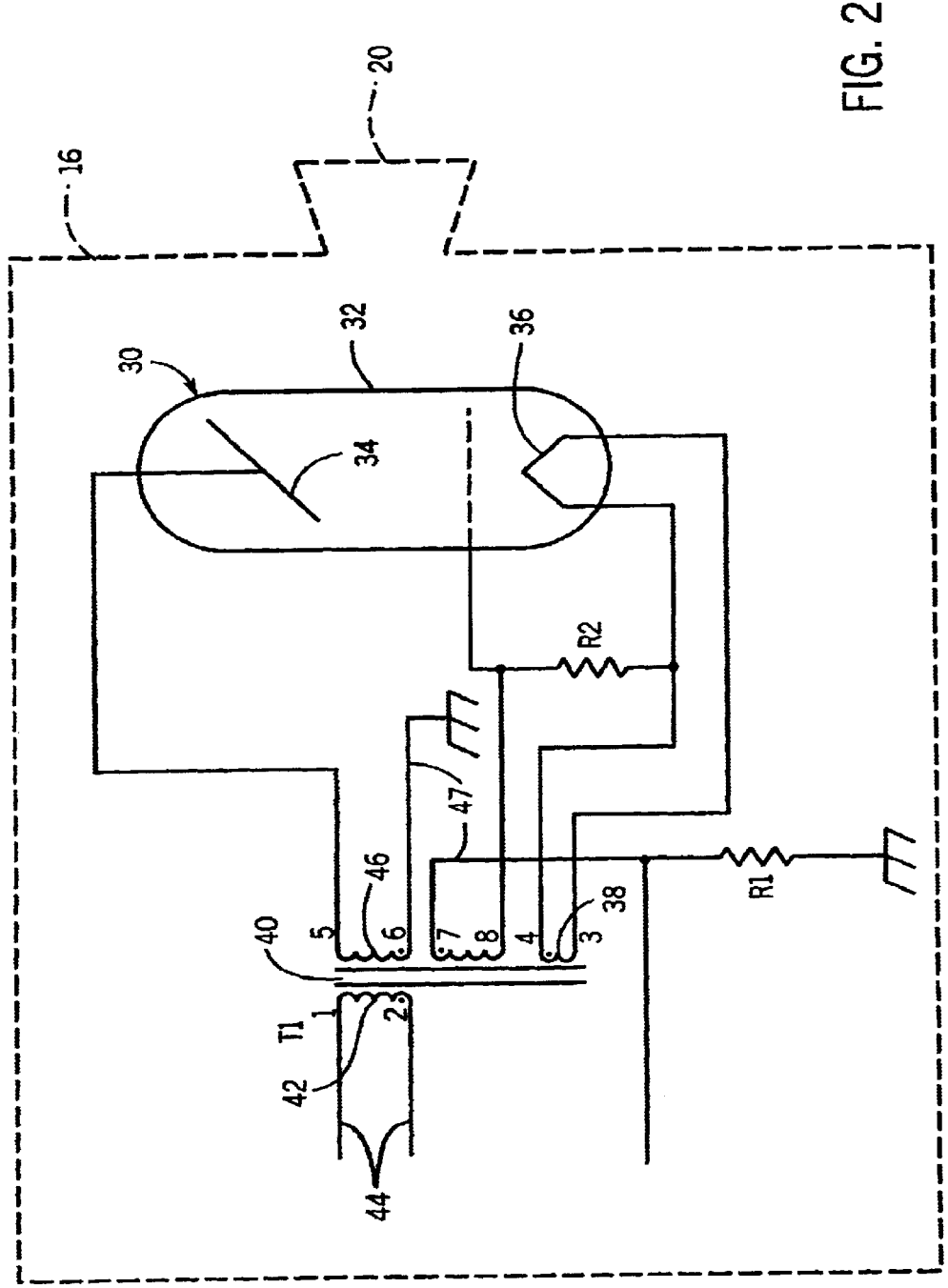
FIG. 2 is a schematic diagram of the electrical circuitry and electrical components in a typical x-ray tube head.

In FIG. 2, electrical components used in x-ray tube head 10 include an x-ray tube 30 comprises a glass envelope 32, with an anode or target 34, an electron emitting filament 36, and a grid 37, all positioned inside. The filament 36 is heated with current delivered from a transformer secondary winding segment 38 relative to a core 40 and a primary winding 42. The primary winding is fed from a pair of leads 44 that extend back through the articulated arm assembly 14 to the control box 12 (FIG. 1). High voltage is applied between anode 34 and electron emitting filament 36 from another secondary winding segment 46. A pair of leads 47 extending from two of the inside legs of the secondary windings connect to the chassis, in effect to ground, through a resistor R1, for the purpose of measuring the tube current. As is well known, grid 37 is used to control the current. A resistor R2 creates a voltage between the grid and the filament, which voltage cuts off the emissions from the tube 30 as a certain predetermined voltage is reached or exceeded. The cone 20, which aims the x-ray tube head 16 toward the proper place on the examination subject's face, is symbolized by dashed lines in FIG. 2.

Figure 3:
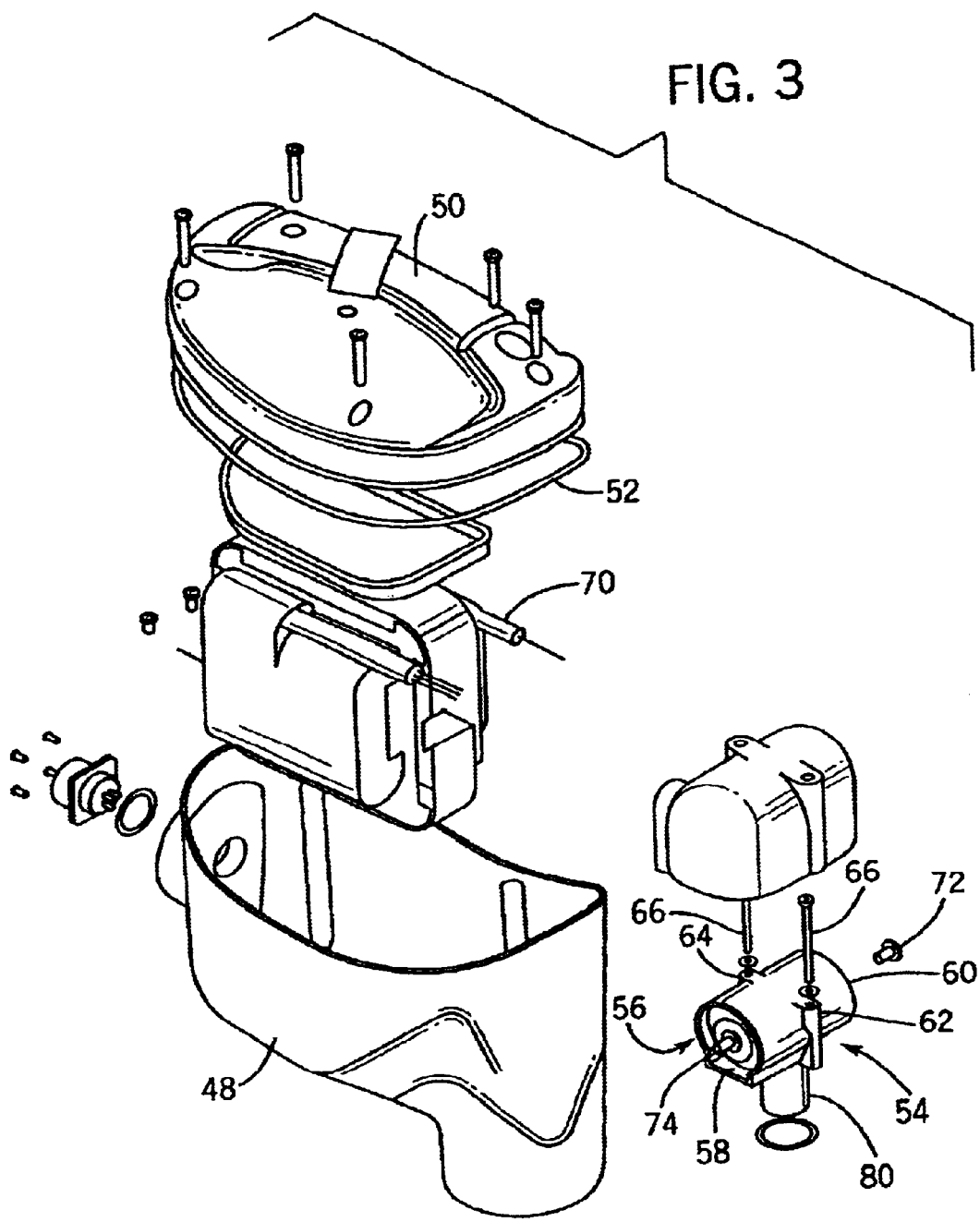
FIG. 3 is an exploded isometric of the x-ray tube head, showing the parts inside.

A vertical section of the x-ray tube head 16 including the new shielding arrangement appears in FIG. 3. The tube head 16 includes a two-piece housing including a deep bottom part 48 and a cover 50. In the embodiment shown, the cover 50 has an integral handle, but the handle may just as well be separate and attached. Bottom part 48 is essentially a deep bowl having sufficient internal volume to accommodate the various electrical components mentioned in connection with FIG. 2. A sealing gasket 52 is applied between the bottom part 48 and the cover 50, which latter parts are held together by means of bolts, not shown, which screw into suitable anchors cast one or the other of the bottom part and cover. Gasket 52 operates to seal the insulating oil inside tube head 16. Any suitable means may be provided for accommodating expansion and contraction of the insulating oil within the tube head 16, such as that shown in the O'Connor patent, the disclosure of which is hereby incorporated by reference.

Cover 50 and lower housing part 48 are preferably made of cast aluminum for the sake of minimizing the weight of the x-ray tube head 16. As is well known, however, aluminum like other lightweight low atomic number elements has very poor x-ray attenuating properties so that additional x-ray shielding must be provided to prohibit stray x-radiation from emanating out of the tube head 16.

Figure 4:
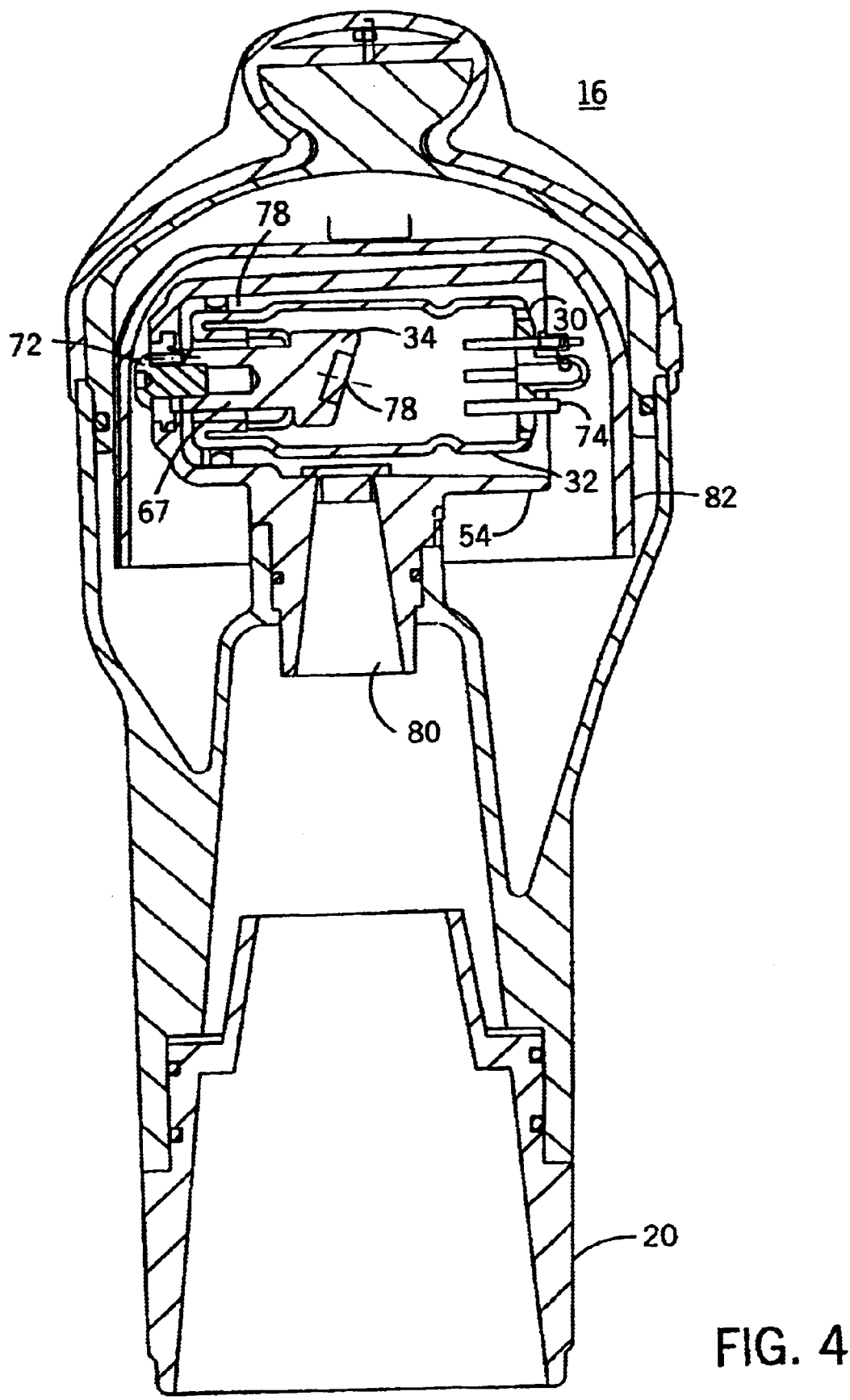
FIG. 4 is a cross sectional view to show the improved shielding components.

FIGS. 3 and 4 illustrate the manner in which the improved shielding of the x-ray tube 30 according to the invention is accomplished. First, the x-ray tube 30 is slid axially into a first shield 54. First shield 54 is generally cylindrical, having an internal bore 56, an open end 58 and a wall 60 at the opposite end which closes the cylinder at that end. First shield 54 has laterally extending flanges 62 and 64 by which the first shield is secured to the inside of the bottom part 48 by any suitable means, such as machine screws 66.

The x-ray tube 30 is secured within the first shield 54 by any suitable means. In the most preferred embodiment, the anode 34 of the x-ray tube 30 is mounted on a metal stem 67 which extends out of the end of the glass x-ray tube envelope 32 and aligns with a bore 68 in the end wall 60 of the cylindrical shield 54. The high voltage lead wire 70 may be removably connected to the x-ray tube anode 34 by any suitable removable means, such as a screw 72 which extends through the bore 68 and engages the stem 67. It will be evident that the x-ray tube 30 is supported in cantilever fashion from first shield 54 by means of the stem 67 and screw 72. The end of the x-ray tube which is adjacent open end 58 of first shield 54 has several connector pins 74 extending from it. Connector wires 76 are connected to these pins, preferably by soldering, for making connections to elements in the x-ray tube 30 as will be evident from consideration of the electrical diagram in FIG. 2. There is an annular free space 78 around x-ray tube envelope 32 to enable circulation of insulating fluid over the x-ray tube envelope to cool and insulate it.

X-rays are produced at a focal spot 78 on the angulated front end of x-ray target or anode 34. First shield 54 has an aperture or cone 80, preferably integrally formed in its wall for permitting the primary x-ray beam to pass from the target 34 toward the exterior of the tube head housing. As described in O'Connor, first shield 54 is formed of a polymeric material impregnated with barium sulfate, although in contradistinction to O'Connor, the inventors have found that polypropylene is the preferred polymer to use in this application. With the open end 58 of the first shield 54 open, however, substantial x-radiation would still escape via that route. As indicated above, various solutions have been proposed, all with substantial disadvantages. The present invention provides for a second shield 82, also substantially cylindrical in shape, but with both ends closed, and with three of the four side aspects closed. This second shield 82 is also formed of polypropylene impregnated with barium sulfate. During assembly, second shield 82 is slid laterally over first shield 54, in a direction transverse to the axis of the tube 30. The open end 58 of the first shield 54 is thereby covered, and in fact all other directions of x-radiation are further attenuated by second shield 82, other than the direction of the cone 80. That direction has other existing means for x-ray attenuation. Second shield 82 is sized with respect to shield 54 to fit loosely over the first shield, so as to again permit circulation of the insulating fluid over the first shield to cool and insulate it.

Providing the second shield 82 of polypropylene impregnated with barium sulfate brings with it numerous advantages over the prior art. Specifically, it achieves the goal of completely eliminating lead shielding from the x-ray tube head 16, as was promised but not delivered by O'Connor. The O'Connor structure required a separate lead shield to cut off the radiation emanating from the open end of the first shield disclosed there. This lead shield, besides adding unduly to the weight of the tube head, also presented problems with its conductivity, whereas the present second shield is sufficiently electrically insulative that the overall size of the tube head housing may be reduced over those tube heads of the prior art, improving the weight advantage of the tube head constructed according to the present invention even more. As indicated above, lead shielding also increased the risk of air bubbles forming in the insulating oil, which could further reduce electrical insulation and radiation shielding, or conversely increase the size of the tube head. Accordingly the present invention provides substantial advantages over the prior art.

While the apparatus hereinbefore described is effectively adapted to fulfill the aforesaid objects, it is to be understood that the invention is not intended to be limited to the specific preferred embodiments of dental x-ray tube head construction set forth above. Rather, it is to be taken as including all reasonable equivalents to the subject matter of the appended claims.

What is claimed is:

1. In a dental x-ray tube head comprising a housing having an x-ray tube mounted therein, the improvement comprising:

an inner shield encasing the x-ray tube and having an aperture through which the primary beam projects, with an open end for connecting wires to the x-ray tube;

an outer shield located within the housing and which fits over the inner shield in such a way as to cover the open end, with clearance for wires connected to the x-ray tube; and wherein both the inner shield and the outer shield are formed of a mixture of polypropylene and barium sulfate.

2. A dental x-ray tube head comprising:

a housing;

an outer shield mounted within the housing;

an inner shield mounted within the outer shield and having an aperture, with an open end, which is covered by the outer shield when mounted; and an x-ray tube mounted in the inner shield;

wherein both the inner shield and the outer shield are formed of a mixture of polypropylene and barium sulfate.

3. A dental x-ray machine comprising:

a tube head connected to a wall unit by means of an articulated arm, said tube head including a housing;

an x-ray tube mounted in the housing;

an inner shield encasing the x-ray tube and having an aperture through which the primary beam projects, with an open end for connecting wires to the x-ray tube; and an outer shield which fits over the inner shield in such a way as to cover the open end, with clearance for wires connected to the x-ray tube, and which fits loosely within the housing;

wherein both the inner shield and the outer shield are formed of a mixture of polypropylene and barium sulfate.

* * * * *